United States Patent
Zhang et al.

(10) Patent No.: US 12,002,209 B2
(45) Date of Patent: Jun. 4, 2024

(54) DIABETES DETECTION DEVICE AND METHOD FOR FORENSIC IDENTIFICATION

(71) Applicant: Academy of Forensic Science, Shanghai (CN)

(72) Inventors: Ji Zhang, Shanghai (CN); Ping Huang, Shanghai (CN)

(73) Assignee: Academy of Forensic Science, Shanghai (CN)

( * ) Notice: Subject to any disclaimer, the term of this patent is extended or adjusted under 35 U.S.C. 154(b) by 0 days.

(21) Appl. No.: 18/355,386

(22) Filed: Jul. 19, 2023

(65) Prior Publication Data
US 2024/0029255 A1    Jan. 25, 2024

(30) Foreign Application Priority Data
Jul. 22, 2022   (CN) .......................... 202210870985.8

(51) Int. Cl.
| | |
|---|---|
| G01N 1/00 | (2006.01) |
| G01N 1/30 | (2006.01) |
| G01N 33/50 | (2006.01) |
| G06T 7/00 | (2017.01) |
| G16H 10/40 | (2018.01) |
| G16H 15/00 | (2018.01) |

(52) U.S. Cl.
CPC ............ *G06T 7/0014* (2013.01); *G01N 1/30* (2013.01); *G01N 33/5091* (2013.01); *G16H 10/40* (2018.01); *G16H 15/00* (2018.01); *G06T 2207/20081* (2013.01); *G06T 2207/20084* (2013.01); *G06T 2207/30084* (2013.01); *G06T 2207/30096* (2013.01)

(58) Field of Classification Search
None
See application file for complete search history.

(56) References Cited

U.S. PATENT DOCUMENTS

2022/0076410 A1 *   3/2022   Georgescu ............... G06N 3/08

FOREIGN PATENT DOCUMENTS

CN            109961059 A            7/2019

* cited by examiner

*Primary Examiner* — Jyoti Nagpaul

(57) ABSTRACT

A diabetes detection method for forensic identification includes the following steps. A sample kidney tissue slice is obtained and processed to obtain initial processing data; the initial processing data are input into a convolutional neural network model for training to obtain target processing data, and training database is obtained based on the target processing data; based on the target processing data in the training database, the sample kidney tissue slice is detected for diabetes, and a forensic identification test report is generated and displayed. The method can solve problems caused by a use of a chemical staining method in a diagnosis of diabetes, provide helps for a forensic pathological cause of death identification, realize scientific identification, ensure the correct trial and judgment of cases, improve the work efficiency of criminal investigators and the accuracy of identification results, and maintain the justice of laws.

6 Claims, 2 Drawing Sheets

DIABETES DETECTION DEVICE AND METHOD FOR FORENSIC IDENTIFICATION

TECHNICAL FIELD

The disclosure belongs to the field of forensic pathology death cause identification, in particular to a diabetes detection device and a diabetes detection method for forensic identification (i.e., medicolegal expertise).

BACKGROUND

Diabetes combined with metabolic diseases is one of the common causes of death in forensic pathology. Due to significant biochemical changes in body fluids after a death, it is difficult to accurately diagnose the diabetes through routine clinical serum testing. Forensic doctors often need to determine whether a deceased had the diabetes before his death with the help of a case, a death process, an autopsy and histopathology, so as to indirectly determine causes of the death.

One of a glomerulus and a kidney tubule is a main pathological structure of the diabetes, and is one of main diagnostic indicators to identify the diabetes. However, resulting lesions can also be seen in other diseases, such as hypertension. It is sometimes difficult to effectively distinguish morphological structures of the hypertension and the diabetes under a routine hematoxylin-eosin (HE) staining. Therefore, the forensic doctors need to conduct other chemical staining methods (such as a Schiff staining) to verify it.

These chemical staining methods are mainly completed manually, which is time-consuming, labor-intensive, and requires a use of many harmful reagents, causing significant damages to experimental personnel and surrounding environments. In addition, a reliability of staining results is related to personal skills of the experimental personnel, and false positive and false negative results often occur.

SUMMARY

In order to solve problems caused by a use of chemical staining methods to diagnose diabetes in the related art, the disclosure provides a following scheme: a diabetes detection device for forensic identification includes a preprocessing system, a model training system and a detection and analysis system.

The preprocessing system is configured (i.e., structured and arranged) to process a sample kidney tissue slice to obtain initial processing data.

The model training system is configured to input the initial processing data into a convolutional neural network model for training to obtain target processing data, and obtain a training database based on the target processing data.

The detection and analysis system is configured to perform diabetes detection on a kidney tissue slice based on the target processing data in the training database, generate and display a forensic identification and detection report.

In an embodiment, the preprocessing system includes a sample grid module, a sample collection module, a data denoising module, and a data collection module.

The sample grid module is configured to perform virtual grid division on a glomerular or renal tubular area in the sample kidney tissue slice to obtain grid areas.

The sample collection module is configured to extract continuous variables that reflect contents and structural characteristics of macromolecular substances in kidney tissues within the grid areas.

The data denoising module is configured to obtain glomerular or renal tubular variables and background variables in the continuous variables.

The data collection module is configured to distinguish positive variables and negative variables from the glomerular or renal tubular variables.

Each of the sample grid module, the sample collection module, the data denoising module, and the data collection module is embodied by software stored in at least one memory and executable by at least one processor.

In an embodiment, the model training system includes a database construction module and a model training module.

The database construction module is configured to label the positive variables and the negative variables to form the training database.

The model training module is configured to train a mathematical model to classify the continuous variables, correct parameters in an architecture of the mathematical model based on the training database, and output a calibration model.

Each of the database construction module and the model training module is embodied by software stored in at least one memory and executable by at least one processor.

In an embodiment, the detection and analysis system includes a sample recognition module, a virtual imaging module, and a display module.

The sample recognition module is configured to identify a glomerular or renal tubular lesion area in the kidney tissue slice, and identify whether glomerular or renal tubular variables in the glomerular or renal tubular lesion area of the kidney tissue slice are positive or negative variables by the calibration model.

The virtual imaging module is configured to observe the glomerular or tubular lesion area, convert the positive variables, the negative variables, and the background variables of the kidney tissue slice into positive pixels, negative pixels, and background pixels, and arrange the positive pixels, the negative pixels, and the background pixels according to virtual grid division to obtain a virtual imaging image.

The display module is configured to generate the forensic identification and detection report based on the virtual imaging image and display the forensic identification and detection report.

Each of the sample recognition module, the virtual imaging module and the display module is embodied by software stored in at least one memory and executable by at least one processor.

A diabetes detection method for forensic identification includes following steps:

obtaining a sample kidney tissue slice and processing the sample kidney tissue slice to obtain initial processing data;

inputting the initial processing data into a convolutional neural network model for training, obtaining target processing data, and obtaining a training database based on the target processing data; and performing diabetes detection on a kidney tissue slice based on the target processing data in the training database, generating and displaying a forensic identification and detection report.

In an embodiment, the obtaining a sample kidney tissue slice and processing the sample kidney tissue slice to obtain initial processing data includes following steps:

performing virtual grid division on a glomerular or renal tubular area in the sample kidney tissue slice to obtain the grid areas;

extracting continuous variables that can reflect contents and structural characteristics of macromolecular substances in kidney tissue within the grid areas;

classifying the continuous variables to obtain the glomerular or renal tubular variables and background variables; and identifying and screening the glomerular or renal tubular variables to obtain positive variables and negative variables.

In an embodiment, the identifying and screening the glomerular or renal tubular variables to obtain the positive variables and negative variables includes following steps:

comparing the sample kidney tissue slice with grid areas of a reference kidney tissue slice, and extracting the positive variables and the negative variables of the glomerular or renal tubular variables in the sample kidney tissue slice based on glomerular or renal tubular lesion area and normal area in the reference kidney tissue slice.

In an embodiment, the reference kidney tissue slice is obtained through a staining treatment. The staining treatment includes one of immunohistochemical staining, special staining, and hematoxylin-eosin (HE) staining. When the reference kidney tissue slice is equal to the sample kidney tissue slice, the reference kidney tissue slice is subjected to staining treatment after extracting the continuous variables. When the reference kidney tissue slice comes from a previous slice or a next slice of the sample kidney tissue slice, the reference kidney tissue slice completes the staining treatment before or after extracting the continuous variables in the sample kidney tissue slice.

In an embodiment, after inputting the initial processing data into a convolutional neural network model for training, obtaining target processing data, and obtaining a training database based on the target processing data, the method further includes following steps:

labelling the positive variables and the negative variables in the glomerular or renal tubular variables to form the training database; and classifying the continuous variables by training a mathematical model, and calibrating parameters in an architecture of the mathematical model based on the training database to obtain a calibration model.

In an embodiment, the performing diabetes detection on a kidney tissue slice according to the target processing data in the training database, generating and displaying a forensic identification and detection report includes following steps:

identifying a glomerular or renal tubular lesion area in the kidney tissue slice, and identifying whether glomerular or renal tubular variables in the glomerular or renal tubular lesion area of the kidney tissue slice are positive or negative variables by the calibration model;

converting the positive variables, the negative variables, and background variables in the glomerular or renal tubular lesion area into positive pixels, negative pixels, and background pixels, and arranging the positive pixels, the negative pixels, and the background pixels according to virtual grid division to obtain a virtual imaging image; and generating the forensic identification and detection report based on the virtual imaging image and displaying the forensic identification and detection report.

The disclosure discloses the following technical effects.

The disclosure provides the diabetes detection device and method for forensic identification, by performing virtual grid division on the sample kidney tissue slice, extracting the continuous variables in the grid areas, screening for the glomerular or renal tubular variables and the background variables from the continuous variables, identifying the positive and negative variables from the glomerular or renal tubular variables, performing construction and training on the model database, generating the calibration model, identifying the glomerular or renal tubular lesion area in the kidney tissue slice by the calibration model to form a virtual imaging image composed of the positive variables, the negative variables, and the background variables. The disclosure establishes a new forensic pathological examination method. The diabetes detection device and method provided by the disclosure can solve problems caused by a use of a chemical staining method in a diagnosis of the diabetes in the related art, and provide helps for a forensic pathological cause of death identification.

The disclosure realizes scientific identification, ensures a correct trial and judgment of cases, improves a work efficiency of criminal investigators, especially forensic personnel, and an accuracy of identification results, maintains a justice of laws.

BRIEF DESCRIPTION OF DRAWINGS

In order to illustrate embodiments of the disclosure or the technical solutions in the related art more clearly, a brief introduction will be made to the drawings needed in the embodiments below. Apparently, the drawings described below are only some of the embodiments of the disclosure. For those skilled in the art, other drawings can be obtained from these drawings without any creative effort.

DETAILED DESCRIPTION OF EMBODIMENTS

In the following, technical solutions in embodiments of the disclosure will be clearly and completely described in conjunction the accompanying drawings. Apparently, the embodiments are only some of embodiments of the disclosure, not all of the embodiments. Based on the embodiments in the disclosure, all other embodiments obtained by those skilled in the art without creative work fall within a scope of a protection of the disclosure.

In order to make objectives, features, and advantages of the disclosure more apparent and understandable, a further detailed description of the disclosure is provided below in conjunction with the accompanying drawings and the specific embodiments.

Figure 1:
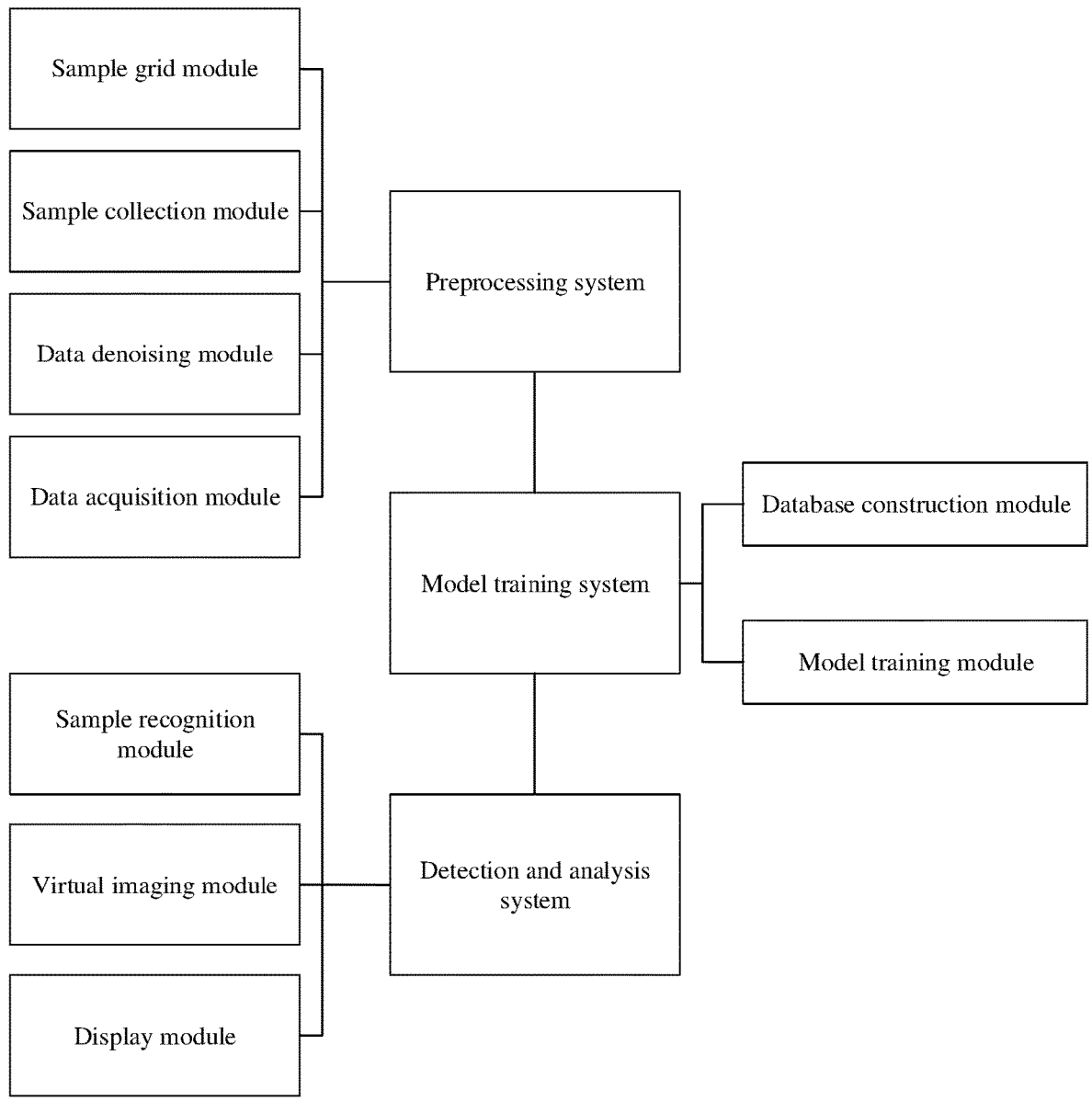
FIG. 1 is a schematic structural diagram of a diabetes detection device for forensic identification according to an embodiment of the disclosure.

As shown in FIG. 1, the disclosure provides a diabetes detection device for forensic identification, including multiple modules as following.

A sample grid module is configured to perform virtual grid division on a glomerular or renal tubular area in a sample kidney tissue slice to obtain m×n grid areas. The m and the n are numbers of grids in a transverse direction and a longitudinal direction of the glomerular or renal tubular area, respectively, and a value of one of the m and the n is an integer value equal to or greater than 0.

A sample collection module is configured to collect (i.e., extract) continuous variables of the sample kidney tissue slice within grid areas. The continuous variables include vibration information of functional groups of macromolecular substances such as proteins, fats, nucleic acids, and sugars, which can reflect contents and structural characteristics of the macromolecular substances.

A data denoising module is configured to determine glomerular or renal tubular variables and background variables from the continuous variables. The glomerular or renal tubular variables are continuous variables containing glomerular or renal tubular structures in the grid areas, and the background variables are continuous variables without the glomerular or renal tubular structures in the grid areas.

A data collection module is configured to distinguish positive variables and negative variables from the glomerular or renal tubular variables, and grid areas corresponding to the positive variables are pathological glomerular or renal tubular structures, and grid areas corresponding to the negative variables are normal glomerular or renal tubular structures.

A database construction module is configured to label the positive variables and the negative variables to form a training database.

A model training module is configured to train a mathematical model to classify the continuous variables, correct parameters in an architecture of the mathematical model using the training database and then output a calibration model. The calibration model can output a probability value of the positive variables by inputting the continuous variables. The probability value is a floating point value greater than 0 and less than 1.

A sample recognition module is configured to identify a glomerular or renal tubular lesion area of a kidney tissue slice. The sample grid module, the sample collection module, and the data denoising module are configured to obtain the glomerular or renal tubular variables and the background variables in the kidney tissue slice, and the calibration model is configured to identify whether the glomerular or renal tubular variables are the positive variables or the negative variables.

A virtual imaging module is configured to observe the glomerular or renal tubular lesion area in the kidney tissue slice, convert the positive variables, negative variables, and background variables obtained from the kidney tissue slice into positive pixels, negative pixels, and background pixels, respectively, and arrange the positive pixels, the negative pixels, and the background pixels according to the virtual grid division to obtain a virtual imaging image.

Figure 2:
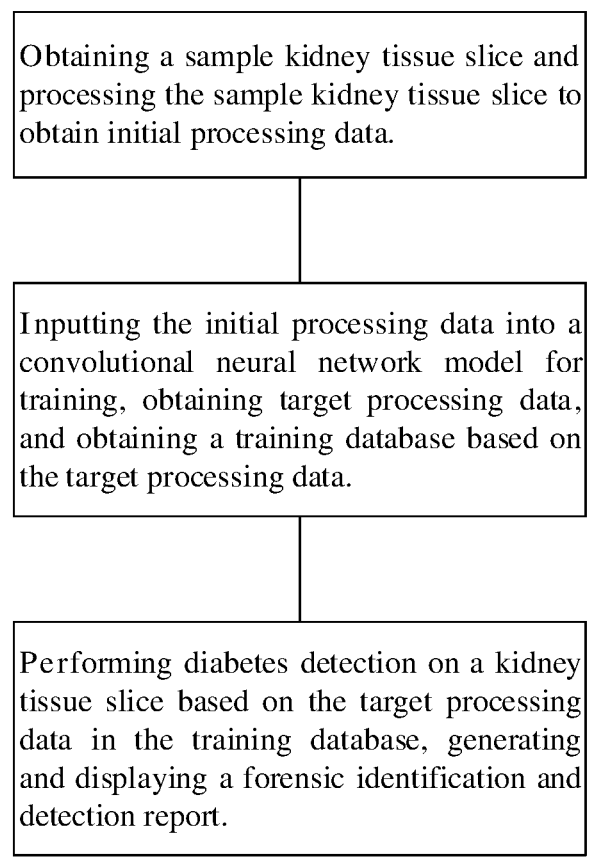
FIG. 2 is a schematic flowchart of a diabetes detection method for forensic identification according to an embodiment of the disclosure.

In an embodiment, as shown in FIG. 2, the disclosure further provides a diabetes detection method for forensic identification, including following steps.

The m×n grid areas are obtained by performing virtual grid division on a glomerular or renal tubular area in a sample kidney tissue slice. The m and the n are numbers of grids in a transverse direction and a longitudinal direction of the glomerular or renal tubular area, respectively, and a value of one of the m and the n is an integer value equal to or greater than 0.

In an embodiment, an area of glomerular or renal tubular structures in the sample kidney tissue slice is identified, and the virtual grid division with an equal size is performed on the area. The grid areas have the same size, and the number of grids in one of a width direction and height direction (a transverse direction and a longitudinal direction) in the glomerular or renal tubular area is greater than 1.

Continuous variables of kidney tissue within the grid areas are collected, and the continuous variables include vibration information of functional groups of macromolecular substances such as proteins, fats, nucleic acids, and sugars, which can reflect contents and structural characteristics of the macromolecular substances.

Glomerular or renal tubular variables and background variables are determined from the continuous variables, the glomerular or renal tubular variables are continuous variables containing glomerular or renal tubular structures in the grid areas, and the background variables are continuous variables without the glomerular or renal tubular structures within the grid areas.

Positive variables and negative variables are distinguished in the glomerular or renal tubular variables, grid areas corresponding to the positive variables are pathological glomerular or renal tubular structures, and grid areas corresponding to negative variables are normal glomerular or renal tubular structures.

The positive variables and the negative variables are labeled to form a training database.

Parameters in an architecture of a mathematical model is corrected using the training database and then a calibration model is output. The calibration model can output a probability value of positive variables by inputting the continuous variables. The probability value is a floating point value greater than 0 and less than 1.

The glomerular or renal tubular variables and the background variables are obtained in a kidney tissue slice (i.e., kidney tissue slice to be predicted), and whether the glomerular or renal tubular variables are the positive variables or the negative variables is identified by the calibration model.

The positive variables, the negative variables, and the background variables obtained from the kidney tissue slice are converted into positive pixels, negative pixels, and background pixels, and the positive pixels, the negative pixels, and the background pixels are arranged according to the virtual grid division to obtain a virtual imaging image.

In an embodiment, one of the following steps is used to identify the glomerular or renal tubular variables and the background variables from the continuous variables.

1. A screening threshold is set to obtain the glomerular or renal tubular variables and the background variables from the continuous variables.
2. The glomerular or renal tubular variables and the background variables are manually obtained from the continuous variables based on a spatial position of the grid areas on the sample kidney tissue slice.

In an embodiment, setting the screening threshold to obtain the glomerular or renal tubular variables and the background variables from the continuous variables includes following two situations.

1. If a quantitative indicator in the continuous variables is lower than the screening threshold, the continuous variables are considered as the background variables.
2. If the quantitative indicator in continuous variables is equal to or greater than the screening threshold, the continuous variables are considered as the glomerular or renal tubular variables.

In an embodiment, the quantitative indicator is a certain data point value in the continuous variables and an area value enclosed by continuous data points in a certain interval in the continuous variables.

In an embodiment, whether biological spectral data obtained from the sample kidney tissue slice comes from the glomerular or renal tubular structures or from the non glomerular and non renal tubular structures is determined by the following two methods.

1. A certain data point value or an area value enclosed by continuous data point values in the spectral data is calculated as the quantitative indicator value. When quantitative indicator value is greater than a specific threshold, the corresponding spectral data are glomerular or renal tubular variables, and the other spectral data are recognized as background variables.

2. Based on continuous slices of test samples or chemical staining results of the test samples, whether corresponding grid areas in the test samples are the glomerular or renal tubular structures, or the non glomerular and non renal tubular structures is determined, thereby the glomerular or renal tubular variables and the background variables are manually determined.

In an embodiment, steps for distinguishing the positive and negative variables from the glomerular or tubular variables are as follows.

The positive variables and the negative variables are extracted based on glomerular or renal tubular lesion area and normal area in a reference kidney tissue slice, respectively. And the grid areas of the reference kidney tissue slice correspond to that of the sample kidney tissue slice one by one.

In an embodiment, the reference kidney tissue slice is obtained after a staining treatment. The reference kidney tissue slice comes from one of following two sources.

1. When the reference kidney tissue slice is equal to the sample kidney tissue slice, the reference kidney tissue slice is subjected to the staining treatment after extracting the continuous variables.
2. When the reference kidney tissue slice comes from one of a previous set or a next slice of the sample kidney tissue slice, the reference kidney tissue slice completes the staining treatment before or after extracting the continuous variables in the sample kidney tissue slice.

In an embodiment, the staining treatment includes any one of immunohistochemical staining, special staining, and hematoxylin-eosin (HE) staining, etc.

In an embodiment, the training database includes training data and classification labels, the training data include the positive variables and the negative variables. The classification labels are integer values of 0 or 1, where the integer value of 1 represents the positive variable in the corresponding training data, and the integer value of 0 represents the negative variable in the corresponding training data.

In an embodiment, the training database is applied to train the mathematical model and the calibration model is formed. When the spectral data are input into the calibration model, the calibration model can output a probability value that the spectral data are positive variables, and the probability value is a floating point value from 0 to 1. The mathematical model architecture includes A module, B module, C module and D module, and output value of the D module is the output value of the mathematical model.

In an embodiment, the A module includes a first convolutional layer including 3 numbers of 3×1 consecutive convolutional kernels, 1 pooling layer, and a second convolutional layer including 3 numbers of 2×1 consecutive convolutional kernels. The first convolutional layer, the pooling layer and the second convolutional layer are connected to one another.

In an embodiment, the B module includes a third convolutional layer including 4 numbers of 3×1 consecutive convolutional kernels, a fourth convolutional layer including 6 numbers of 2×1 consecutive convolutional kernels, and a fifth convolutional layer including 3 numbers of 5×1 consecutive convolutional kernels. The third convolutional layer, the fourth convolutional layer and the fifth convolutional layer are connected to one another.

In an embodiment, the C module is configured to form a vector value by concatenating multiple vector values. The vector values include a vector value of an output value of the A module, a vector value of an output value of the convolutional layer including the 4 numbers of 3×1 consecutive convolutional kernels in the B module, a vector value of the convolutional layer including the 6 numbers of 2×1 consecutive convolutional kernels in the B module, a vector value of an output value of the B module.

In an embodiment, an output value of the D module includes an output value of the C module, and the D module includes a fully connected layer with dimension 64, and a fully connected layer with dimension 2.

In an embodiment, identifying whether the glomerular or renal tubular variables are positive variables or negative variables by the calibration model includes following steps.

The glomerular or renal tubular variables and the background variables are obtained in the kidney tissue slice, the calibration model is applied to obtain a probability value of whether the glomerular or renal tubular variables are the positive variables, and the positive variables and the negative variables are determined based on the specific threshold.

The positive variables, the negative variables, and the background variables obtained from the kidney tissue slice are arranged to the corresponding grid areas according to three different pixel values to form a virtual imaging image, which can more intuitively observe the glomerular or renal tubular lesion area. Numbers of pixels in the height direction and the width direction in the virtual imaging image are consistent with numbers of grids in the glomerular or renal tubular area of the kidney tissue slice.

The glomerular or renal tubular variables are input into the calibration model and the probability value of the glomerular or renal tubular variables as the positive variables is output. When the probability value is equal to or greater than the specific threshold, the continuous variables are considered as the positive variables, otherwise the continuous variables are the negative variables, and the specific threshold is a floating point value greater than 0 and less than 1.

In an embodiment, a width of the virtual imaging image is composed of m pixels, and a height of the virtual imaging image is composed of n pixels.

The embodiments are only a description of preferred embodiments of the disclosure, not a limitation of a scope of the disclosure. Without departing from a spirit of a design of the disclosure, various modifications and changes made by those skilled in the art to the technical solution of the disclosure shall fall within the scope of a protection determined by the claims of the disclosure.

What is claimed is:

1. A diabetes detection method for forensic identification, comprising:
   obtaining a sample kidney tissue slice and processing the sample kidney tissue slice to obtain initial processing data;
   inputting the initial processing data into a convolutional neural network model for training, obtaining target processing data, and obtaining a training database based on the target processing data; and
   performing diabetes detection on a kidney tissue slice based on the target processing data in the training database, generating and displaying a forensic identification and detection report;
   wherein the obtaining a sample kidney tissue slice and processing the sample kidney tissue slice to obtain initial processing data comprises:
   performing virtual grid division on a glomerular or renal tubular area in the sample kidney tissue slice to obtain grid areas;

extracting continuous variables that reflect contents and structural characteristics of macromolecular substances including proteins, fats, nucleic acids, and sugars in kidney tissues within the grid areas, wherein the continuous variables represent information that reflects the contents and the structural characteristics of the macromolecular substances;

classifying the continuous variables to obtain glomerular or renal tubular variables and background variables, comprising:

setting a screening threshold;

obtaining a quantitative indicator corresponding to the continuous variables; wherein the quantitative indicator is a data point value in the continuous variables or an area value enclosed by continuous data points in the continuous variables;

considering, in response to the quantitative indicator being lower than the screening threshold, the continuous variables as the background variables; and considering, in response to the quantitative indicator being equal to or greater than the screening threshold, the continuous variables as the glomerular or renal tubular variables; and identifying and screening the glomerular or renal tubular variables to obtain positive variables and negative variables, wherein grid areas corresponding to the positive variables are pathological glomerular or renal tubular structures, and grid areas corresponding to the negative variables are normal glomerular or renal tubular structures.

2. The diabetes detection method for forensic identification as claimed in claim 1, wherein the identifying and screening the glomerular or renal tubular variables to obtain the positive variables and negative variables comprises:

comparing the sample kidney tissue slice with grid areas of a reference kidney tissue slice, and extracting the positive variables and the negative variables of the glomerular or renal tubular variables in the sample kidney tissue slice based on glomerular or renal tubular lesion area and normal area in the reference kidney tissue slice.

3. The diabetes detection method for forensic identification as claimed in claim 2, wherein the reference kidney tissue slice is obtained through a staining treatment;

wherein the staining treatment comprises one of immunohistochemical staining, special staining, and hematoxylin-eosin (HE) staining;

wherein when the reference kidney tissue slice is equal to the sample kidney tissue slice, the reference kidney tissue slice is subjected to the staining treatment after extracting the continuous variables; and wherein when the reference kidney tissue slice comes from a previous slice or a next slice of the sample kidney tissue slice, the reference kidney tissue slice completes the staining treatment before or after extracting the continuous variables in the sample kidney tissue slice.

4. The diabetes detection method for forensic identification as claimed in claim 3, wherein after inputting the initial processing data into a convolutional neural network model for training, obtaining target processing data, and obtaining a training database based on the target processing data, the method further comprises:

labeling the positive variables and the negative variables in the glomerular or renal tubular variables to form the training database; and classifying the continuous variables by training a mathematical model, and calibrating parameters in an architecture of the mathematical model based on the training database to obtain a calibration model.

5. The diabetes detection method for forensic identification as claimed in claim 4, wherein the performing diabetes detection on a kidney tissue slice according to the target processing data in the training database, generating and displaying a forensic identification and detection report, comprises:

identifying a glomerular or renal tubular lesion area in the kidney tissue slice, and identifying whether glomerular or renal tubular variables in the glomerular or renal tubular lesion area of the kidney tissue slice are positive or negative variables by the calibration model;

converting the positive variables, the negative variables, and background variables in the glomerular or renal tubular lesion area into positive pixels, negative pixels, and background pixels, and arranging the positive pixels, the negative pixels, and the background pixels according to virtual grid division to obtain a virtual imaging image; and generating the forensic identification and detection report based on the virtual imaging image and displaying the forensic identification and detection report.

6. The diabetes detection method for forensic identification as claimed in claim 5, wherein the identifying whether glomerular or renal tubular variables in the glomerular or renal tubular lesion area of the kidney tissue slice are positive or negative variables by the calibration model, comprises:

obtaining a probability value of the glomerular or renal tubular variables as the positive variables by the calibration model, and obtaining a threshold; wherein the threshold is a floating point value greater than 0 and less than 1;

determining, in response to the probability value being equal to or greater than the threshold, the glomerular or renal tubular variables as the positive variables; and determining, in response to the probability value being lower than the threshold, the glomerular or renal tubular variables as the negative variables.

* * * * *